(12) United States Patent
Povinelli et al.

(10) Patent No.: US 7,308,301 B2
(45) Date of Patent: Dec. 11, 2007

(54) METHOD AND APPARATUS FOR DETECTING A CARDIAC ARRHYTHMIA

(75) Inventors: Richard J. Povinelli, Milwaukee, WI (US); Felice M. Roberts, Oconomowoc, WI (US); Jack E. Lohman, Colgate, WI (US)

(73) Assignee: Marquette University, Milwaukee, WI (US)

( * ) Notice: Subject to any disclaimer, the term of this patent is extended or adjusted under 35 U.S.C. 154(b) by 286 days.

(21) Appl. No.: 10/939,146

(22) Filed: Sep. 10, 2004

(65) Prior Publication Data

US 2005/0033191 A1 Feb. 10, 2005

Related U.S. Application Data

(63) Continuation-in-part of application No. 10/758,917, filed on Jan. 16, 2004, now Pat. No. 7,117,031, which is a continuation-in-part of application No. 09/827,551, filed on Apr. 6, 2001, now Pat. No. 6,701,183.

(51) Int. Cl.
*A61B 5/04* (2006.01)

(52) U.S. Cl. .................................. 600/515; 600/508
(58) Field of Classification Search ................. 600/515
See application file for complete search history.

(56) References Cited

U.S. PATENT DOCUMENTS

| 5,351,696 A | * | 10/1994 | Riff et al. | ................... 600/515 |
| 5,645,070 A | * | 7/1997 | Turcott | ....................... 600/515 |
| 5,815,413 A | * | 9/1998 | Hively et al. | ............... 702/191 |

* cited by examiner

*Primary Examiner*—Carl Layno
*Assistant Examiner*—Brian T. Gedeon
(74) *Attorney, Agent, or Firm*—Quarles & Brady LLP (57) ABSTRACT

A method is provided for detecting whether a patient is likely experiencing a cardiac arrhythmia. The method includes acquiring baseline ECG samples that exhibit an arrhythmia that is to be detected, and a baseline arrhythmia-free ECG sample. Each acquired baseline ECG sample is manipulated to determine an equation that describes a reconstructed phase space related to the sample. Next, an ECG sample to be tested is acquired, and a reconstructed phase space is mapped. Finally, it is determined which of the equations most accurately describes the reconstructed phase space of the ECG sample to be tested.

32 Claims, 9 Drawing Sheets

METHOD AND APPARATUS FOR DETECTING A CARDIAC ARRHYTHMIA

CROSS-REFERENCE TO RELATED APPLICATIONS

This application is a continuation-in-part of U.S. patent application Ser. No. 10/758,917 filed Jan. 16, 2004 now U.S. Pat. No. 7,117,031 which is, in turn, a continuation-in-part of U.S. patent application Ser. No. 09/827,551 filed Apr. 6, 2001 now U.S. Pat. No. 6,701,183, the disclosure of each of which is hereby incorporated by reference as if set forth in its entirety herein.

STATEMENT REGARDING FEDERALLY SPONSORED RESEARCH OR DEVELOPMENT

--

BACKGROUND OF THE INVENTION

The present invention relates to electronic devices for detecting a cardiac arrhythmia and in particular to a device providing improved patient mobility and reliable long-term monitoring.

The human heart normally beats anywhere from 60 to 80 beats per minute when a person is at rest. Diagnosis of cardiac arrhythmias normally requires that a qualified professional review an electrocardiograph (ECG) in which the electrical impulses from the heart are recorded and displayed in chart form. The electrical impulses are measured by electrodes attached at a number of locations to the patient's chest. Certain episodes of cardiac arrhythmias, although serious, can be unnoticed by the patient. For example, it is desirable that chronic atrial fibrillation be treated within 48 hours of its onset.

One possible solution is the use of a "cardiac event recorder", a portable ECG recording device carried by the patient and communicating with electrodes worn under the patient's clothing and adhesively attached to the patient's skin. Such recorders may provide algorithms for monitoring the ECG signal and may report to the users, for example, that atrial fibrillation has begun. Recorders of this type may also record a rolling "window" of ECG data using solid state computer memory. In this latter case, the recorded ECG data may be transmitted over phone lines, the Internet, or the like for review by a qualified physician.

Unfortunately, the cardiac event recorder is not a practical tool for providing a warning of the onset of certain cardiac arrhythmias that can occur unexpectedly at any time in later life. The need for the patient to carry the cardiac event monitor about during the day and the continuous attachment of electrodes is impractical for long term monitoring that may span decades.

What is therefore needed is a less cumbersome, and more patient-friendly, apparatus and method for detecting cardiac arrhythmias than currently achieved.

BRIEF SUMMARY OF THE INVENTION

In accordance with one aspect of the invention, a method is provided for detecting a likelihood that a patient is experiencing one of several arrhythmias. The method includes a first step of acquiring baseline ECG samples, each of which exhibiting an arrhythmia to be detected and a baseline arrhythmia-free ECG sample. Next, a reconstructed phase space related to each acquired baseline ECG sample is mapped. The method next includes the step of determining at least one equation describing the reconstructed phase space for each acquired baseline ECG sample. An ECG sample to be tested is then acquired, and a reconstructed phase space is mapped for the ECG sample to be tested. Next, the method determines which of the equations most accurately describes the reconstructed phase space related to the ECG sample to be tested.

The aspects may not apply to all embodiments of the inventions and are not intended to define the scope of the invention, for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

DETAILED DESCRIPTION OF THE PREFERRED EMBODIMENT

Figure 1:
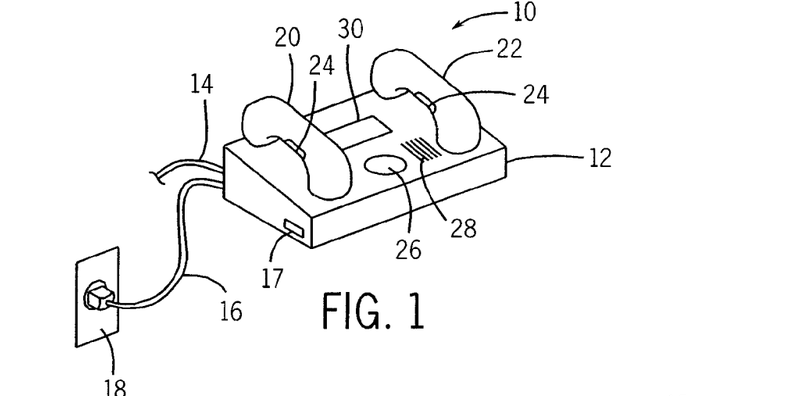
FIG. 1 is a perspective view of a device for monitoring at least one of a plurality of arrhythmias as constructed according to the present invention showing handles for supporting electrodes to be grasped by the patient, a patient display, and connections for receiving power and communicating on the phone system.

Referring now to FIG. 1, a cardiac arrhythmia monitor 10 includes a housing 12 suitable for sitting on a tabletop, such as a nightstand or dresser. Monitor 10 is preferably portable and hence battery powered. Alternatively, a power cord 14 can extend from monitor 10 and be plugged into a wall outlet (not shown). A phone line connector cord 16 extends from monitor 10 and can plugged into a conventional phone jack 18. A programming connector 17 is also provided to allow programming of the monitor 10 by a qualified healthcare professional prior to use by a patient as will be described. While monitor 10 is particularly well-suited for detecting atrial fibrillation, monitor 10 can also be used to detect a plurality of other cardiac arrhythmias, as is described below.

The upper surface of the housing 12 includes a right and left handle, 20 and 22 respectively, providing on their undersurfaces momentary contact electrodes 24. Momentary contract electrodes 24 may be bare metal surfaces, such as stainless steel plates, and are distinguished from conventional ECG electrodes by the absence of adhesive or other methods of affixing the electrodes to the patient's skin and retaining them there. The electrodes 24 each contact one of the patient's hands when the patient grasps the left handle 20 in the patient's left hand and the right handle 22 in the patient's right hand. Those skilled in the art will appreciate that alternative electrode materials could be used. Alternatively still, electrodes 24 can be capacitively coupled using techniques well known in the art, and described in U.S. Pat. No. 4,922,375, the disclosure of which is hereby incorporated by reference.

One or more indicator lights 26 are positioned on the top surface of the housing 12 to provide an indication to the patient of the condition of the patient's heartbeat. In the preferred embodiment, the indicator light 26 shows green when no irregularities are found in the patient's heartbeat and red when a cardiac arrhythmia is detected. The red light can be constantly illuminated or blinking depending on the cardiac arrhythmia that has been detected. For instance, detecting either a prolonged QT interval or a ventricular tachycardia will prompt a blinking red light.

A grating 28 in the housing 12 may provide for communication of an audio, such as a tone or the message from an underlying speaker (not shown in FIG. 1). The audio may be used to remind the patient to take a reading or to provide instructions to the patient and/or as a redundant indication of the detection of an arrhythmia augment the indicator light 26. An LCD display 30 may provide for a graphic output including text instructions to the patient as will be described below. Alternatively, monitor 10 may include a motor (not shown in FIG. 1) that vibrates either along with, or instead of, the audio and/or LCD display 30.

Figure 2:
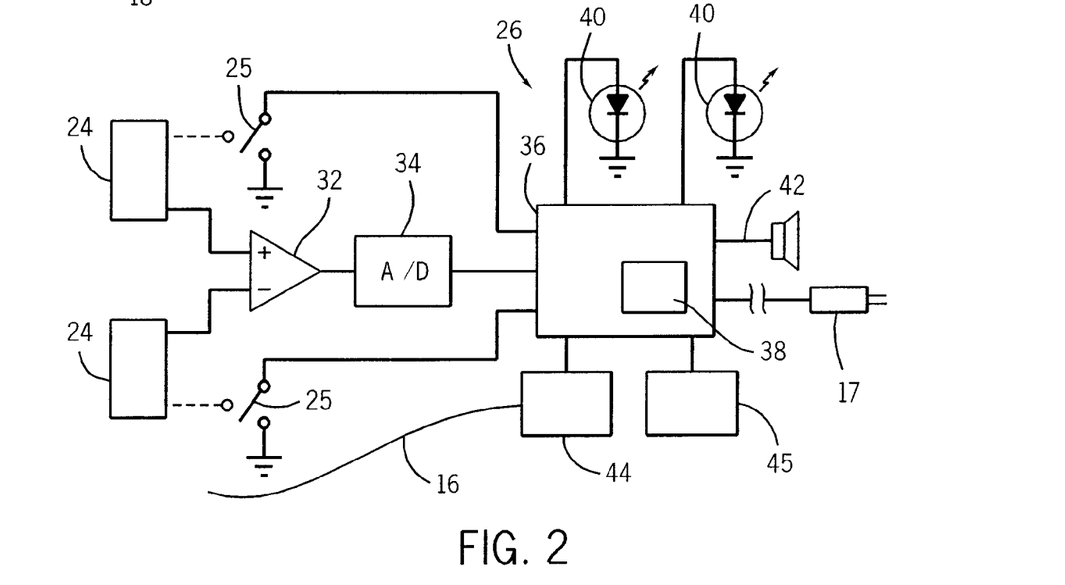
FIG. 2 is a block diagram of the components of the device of FIG. 1 showing connection of the electrodes through an ECG amplifier to an analog to digital converter to be received and processed by a microcontroller having memory for storage of ECG signals.

Referring now to FIG. 2, the electrodes 24 are received by an ECG amplifier 32 of a type well known in the art and providing for noise rejection and ground referencing of the ECG signal. The output of the ECG amplifier 32 is provided to an analog to digital converter 34 to be converted to a set of digital signals that may be received by microcontroller 36.

Microcontroller 36 combines a microprocessor with one or more input/output ports and incorporates both volatile and non-volatile memory 38, the former holding programming and baseline data and the latter providing a space for storing ECG signals. Two of the input/output ports are connected to red and green indicator lamps 40 providing light sources for the indicator light 26. A third input/output port is connected to a speaker or piezoelectric audio transducer 42 for providing tones or voice messages as may be appropriate to remind the patient to take a measurement of his or her heartbeat and/or to provide messages for operation of monitor 10. A fourth set of input/output lines are connected to modem 44 which is connected to phone line connector cord 16 for communication of data over the telephone lines using standard data communication protocols. The modem may either be connected directly to the telephone lines, or may alternatively be connected to a speaker that would output acoustic signals into a telephone handset for the transmission of ECG data. While telephone lines are implemented in accordance with the preferred embodiment, it should be easily appreciated that the data transfer could be accomplished using one of many well-known alternative communication systems, such as the Internet, as will be described in more detail below. A fifth set of input/output lines is provided to the programming connector 17 such as allows programming of various parameters of operation of the monitor 10 as will be described below. Finally, a sixth set of input/output lines is connected to a motor 45 that vibrates as appropriate to remind the patient to take a measurement of his or her heartbeat and/or to provide an indication that a cardiac arrhythmia has been detected.

Figure 3:
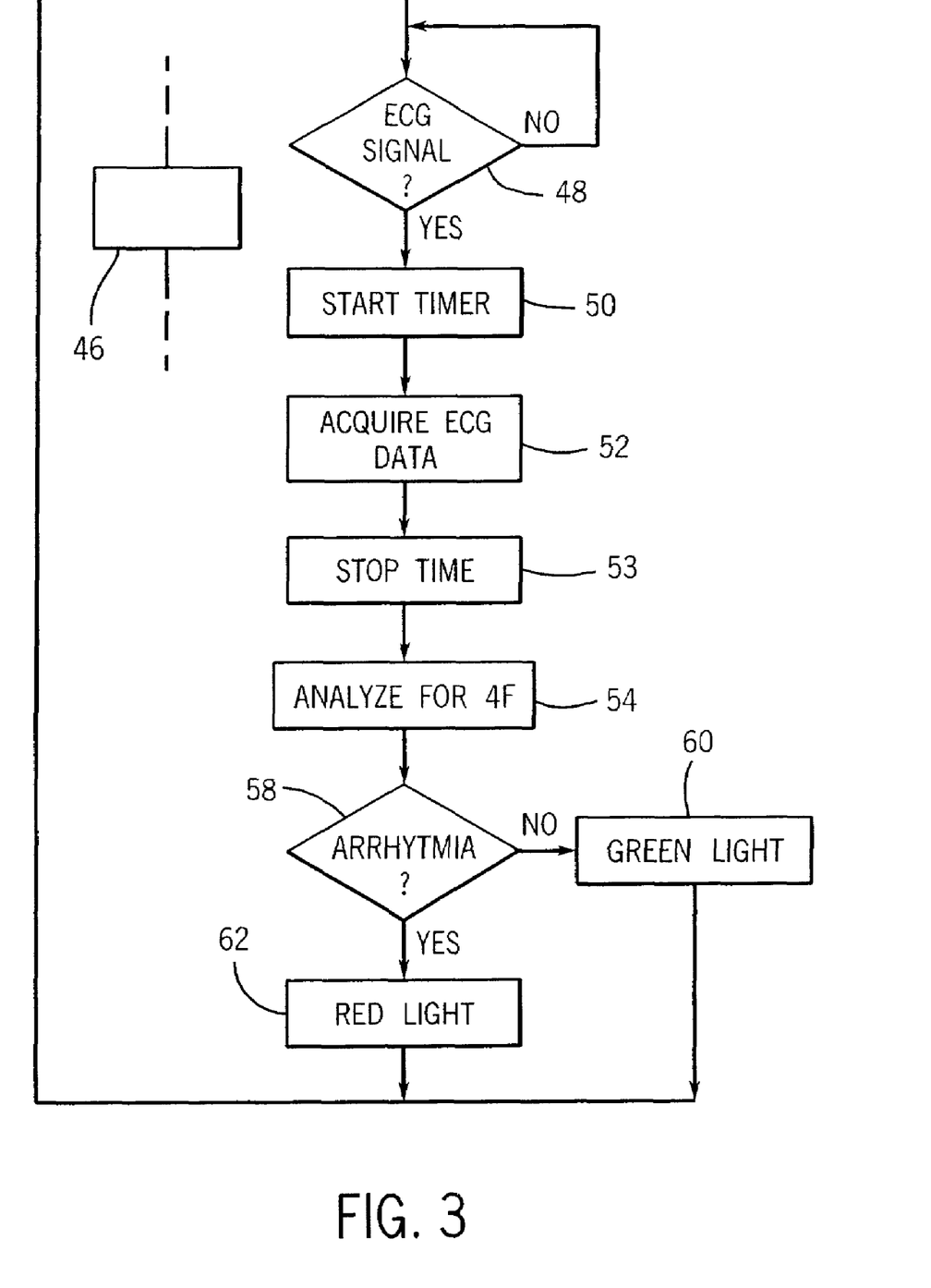
FIG. 3 is a flow chart showing steps executed by the microcontroller of FIG. 2 in processing ECG signals from the patient.

Referring now to FIG. 3, the program of the microcontroller 36 may include an alarm clock routine 46 executing in parallel with the main program to provide alarm clock type functions well known in the art and, in particular, a tone at a regular time to remind the patient to use the monitor 10. This alarm clock routine operates according to well-known algorithms and the alarm time (and current time) may be set by attaching the monitor 10 to a programming computer via the programming connector 17. Alternatively, setting controls (not shown) may be provided on top of the housing 12 in the manner of a conventional electronic alarm clock.

The program of the microcontroller 36 also executes a loop indicated by decision block 48 detecting an ECG signal such as would indicate a connection by the patient's hands to the electrodes 24. This loop may simply detect the presence of an ECG signal detected by monitoring the output of the analog to digital converter 34 or may detect a resistance drop between the electrodes using separate circuitry well known in the art.

Upon placement of the user's hands on the electrodes 24, the microcontroller 36 starts a timer as indicated by process block 50 and may provide a text display through LCD display 30 or a voice message through audio transducer 42 to the user indicating that ECG acquisition is being performed and instructing the user to retain his or her hands in position until the full elapsed time has expired. The timer value may also be displayed.

Following the starting of the timer, as indicated by process block 52, data is acquired by progressively taking samples from the analog to digital converter 34 and storing them in memory 38. The present invention recognizes that stored data can be analyzed to detect a plurality of noteworthy arrhythmias.

Figure 8:
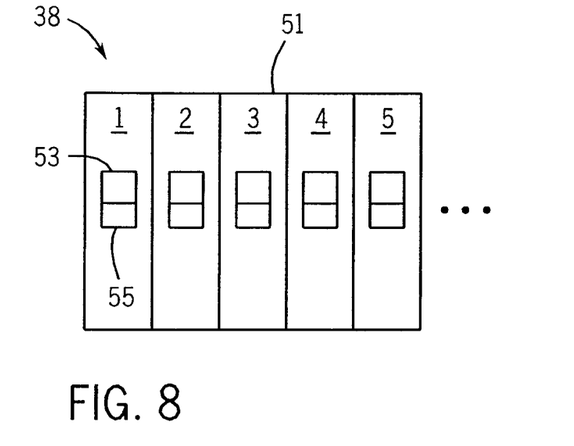
FIG. 8 is a schematic diagram of a cascading memory constructed in accordance with the preferred embodiment.

Referring now to FIG. 8, a cascading memory 51 is provided in volatile memory in accordance with the preferred embodiment. Memory 51 includes a plurality of storage locations (anywhere from 5 to 100 slots in accordance with the preferred embodiment), each storage location storing a sample of acquired ECG data. Each acquired ECG data sample is tagged, either by microcontroller 36 or locally in memory 38, and stored in a memory storage location (e.g., one of slots 1-5), which is determined to be that storage location currently holding the oldest sample of volatile ECG data, as determined by the tag 55 associated with the data. The tag can either be a time stamp, an indicator that can be compared to indicators of the other stored data to determine the chronological order of the stored data, or any other suitable age indicator. In accordance with the preferred embodiment, the tag is a timestamp including a number of ticks that occur at a predetermined time (e.g., every minute). The oldest ECG data would then be identified by the timestamp with the greatest number of ticks. Accordingly, oldest ECG data is constantly replaced with newly acquired data.

Alternatively, only that ECG data indicating a likely arrhythmia can be stored in the storage locations. Alternatively still, all ECG data can be stored, whereby the tag would include an indication of whether the stored ECG data is normal or whether it indicates an arrhythmia and, if so, which arrhythmia.

The cascading memory thus enables the patient to transmit recent historical ECG data along with the recently acquired ECG sample to a physician or other evaluating personnel, along with the previously stored ECG data, if desired.

In addition to, or separately from, the cascading memory scheme, the present invention recognizes the advantages in storing baseline data for a given patient either in nonvolatile memory, or in volatile memory in a memory storage location (e.g., "slot 0") that is not erased during normal operation. The baseline data is preferably stored in FLASH memory, such that the data would not be erased upon a battery changes. The baseline data can include one or more of various data samples, including a baseline ECG data sample for the patient. The baseline ECG data can be compared with subsequent ECG samples to determine whether the patient is suffering from a prolonged QT interval, as will become more apparent form the description below. The shape of the QRS complex for the baseline ECG data can also be stored, either as the waveform itself or by storing critical data points that adequately describe the waveform shape. It should furthermore be appreciated that baseline data samples can be stored in nonvolatile memory on a regular basis (for example once every year) to identify trends in the patient's ECG data.

Other baseline data can be stored and compared when analyzing a patient's real-time ECG data in order detect whether a patient is experiencing a cardiac arrhythmia. Moreover, if an arrhythmia is detected, the baseline data can identify the type of cardiac arrhythmia among a list of potential arrhythmias being tested for. This type of baseline data is referred to as "sample" baseline data throughout this description, and is described in more detail below.

A stop timer signal, as indicated by process block 53, concludes the acquisition of ECG data and signals the patient that he or she need no longer grasp the electrodes. The time interval for the acquisition of ECG signals is normally between several seconds (e.g., 2-3 seconds) and a few minutes (e.g., five minutes) and substantially less than a day, as is typical for use with conventional cardiac evaluation monitors.

Figure 9A:
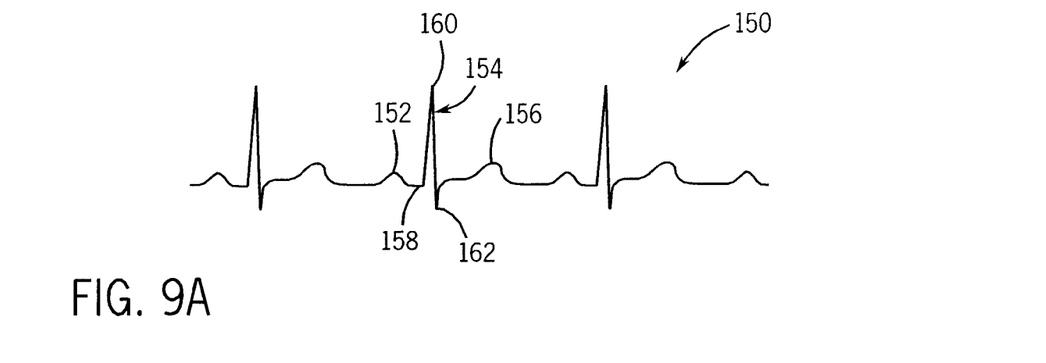
FIG. 9A is a schematic diagram of an arrhythmia-free ECG signal.
Figure 9B:
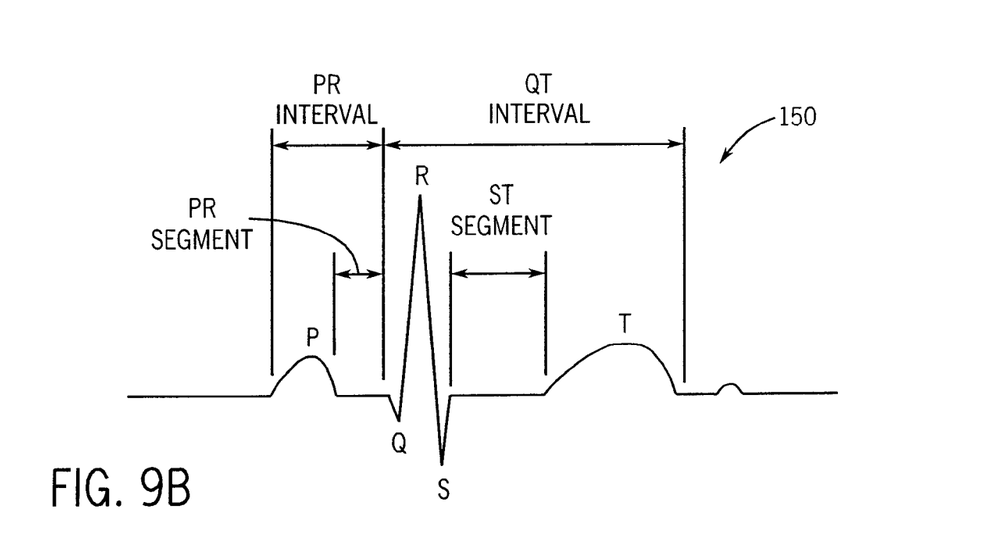
FIG. 9B is the diagram illustrated in FIG. 9A with annotations to demonstrate various parts of the ECG signal.

Referring to FIGS. 9A-B, a normal ECG signal 150 is illustrated and includes a P wave 152 followed by a QRS 154 complex, which is followed by a T wave 156. The QRS complex includes an initial base (Q) 158, a peak (R) 160, and a final base (S) 162. The P wave 152 has amplitude that is approximately equal to 10% of the amplitude of peak 160, while the T wave 156 has amplitude that is approximately equal to 25% of the amplitude of the peak 160.

Figure 10:
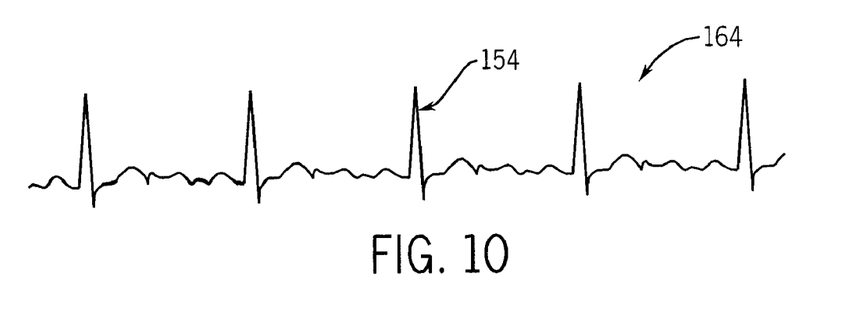
FIG. 10 diagram similar to FIG. 9, but illustrating atrial fibrillation.

A number of arrhythmias can be diagnosed based on a patient's ECG data. Supraventricular tachycardia, for instance, includes atrial fibrillation and atrial flutter. Atrial fibrillation develops when a disturbance in the electrical signals causes the two upper atrial chambers of the heart to quiver rather than pump correctly. When the quivering occurs, not all of the blood is forced out of the heart's chambers. The blood can pool inside the atrium and, at times clot. Blood clots can cause a number of health problems, including a stroke if they break away and block an artery in the brain. As illustrated in FIG. 10, an ECG signal 164 of a person experiencing atrial fibrillation does not present a P wave. Moreover, the R-R interval (defined as the length of time between R peaks of adjacent QRS complexes) is irregular when a patient is experiencing atrial fibrillation.

Figure 11:
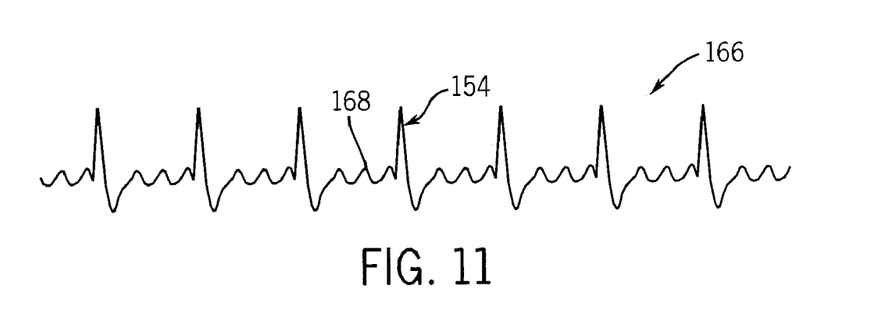
FIG. 11 is a diagram similar to FIG. 9, but illustrating atrial flutter.

Atrial flutter occurs when the atria are stimulated to contract regularly at an accelerated rate (e.g., 200-350 beats per minute), typically as the result of electrical impulses traveling in a circular fashion around the atria. As illustrated in FIG. 11, atrial flutter waves (F waves) are present instead of P waves in an ECG signal demonstrating atrial flutter 166. F waves 168 are generally larger than P waves, and present a saw-toothed waveform. A whole number fixed ratio of flutter waves to QRS complexes can typically be observed, for instance 2:1, 3:1 or 4:1

It should be appreciated that the present device, while well-suited for the detection of atrial fibrillation and atrial flutter, can also detect other cardiac abnormalities if they happen to be occurring at the time of the reading. Patients known to be predisposed to some of these abnormalities, which are more serious and require more immediate attention than atrial fibrillation, should be monitored regularly, as opposed to using the momentary contacts of the present invention. Nevertheless, for patients who do not know about these abnormalities, it is desirable for the present invention to also detect these more serious conditions when monitoring for less urgent arrhythmias, such as atrial fibrillation, atrial flutter, or the like.

Figure 12:
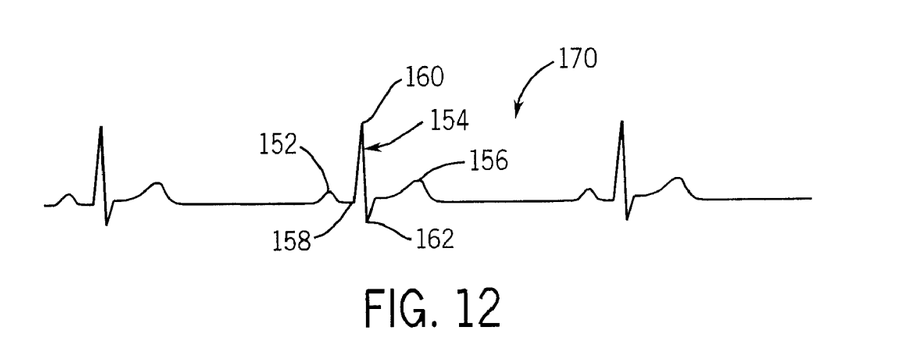
FIG. 12 is a diagram similar to FIG. 9, but illustrating bradycardia.

Bradycardia occurs when a person's heartbeat is slowed (typically less than 60 beats per minute), causing the patient to feel fatigued, dizzy, and lightheaded. Bradycardia can also cause fainting spells. As illustrated in FIG. 12, the ECG signal demonstrating a bradycardia rhythm 170 is similar to a normal rhythm, except that the R-R interval is longer and, occasionally, the P-waves might be abnormally wide.

Figure 13:
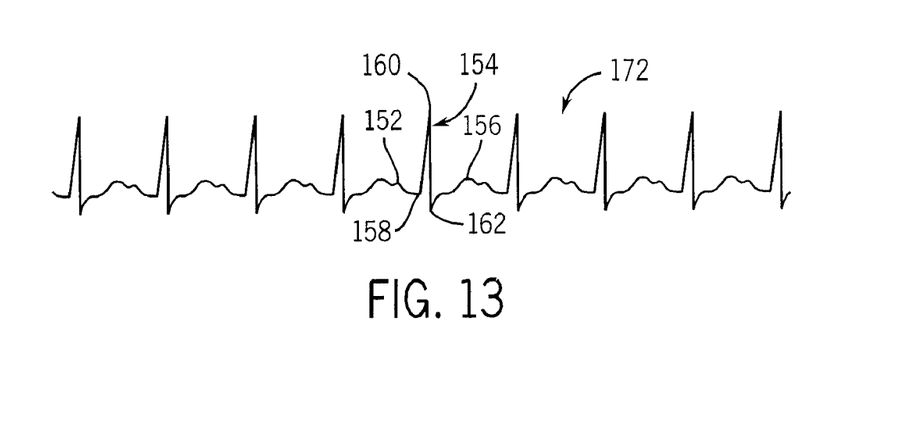
FIG. 13 is a diagram similar to FIG. 9, but illustrating atrial tachycardia.

Atrial tachycardia occurs when the rhythm is accelerated (e.g., greater than 100 beats per minute). This condition can cause inefficient blood circulation, thereby causing a patient to feel palpitations, rapid heart action, dizziness, and lightheadedness. As illustrated in FIG. 13, the rhythm 172 for atrial tachycardia is similar to normal ECG rhythm 150 with the exception that the RR interval is shorter (e.g., less than 0.6 seconds). At very rapid rates, the P-waves might become superimposed on the preceding T waves such that the P waves are obscured by T waves.

Ventricular pauses are detected upon an abrupt halting of the heart rate (i.e., one or more dropped heartbeats) and can be detected when the RR interval is greater than twice a predetermined "normal" value.

Premature ventricular contractions (PVC's) occur when the ventricles beat prematurely before the normal electrical activation sequence of the heart has occurred, which can cause palpitations.

Figure 14A:
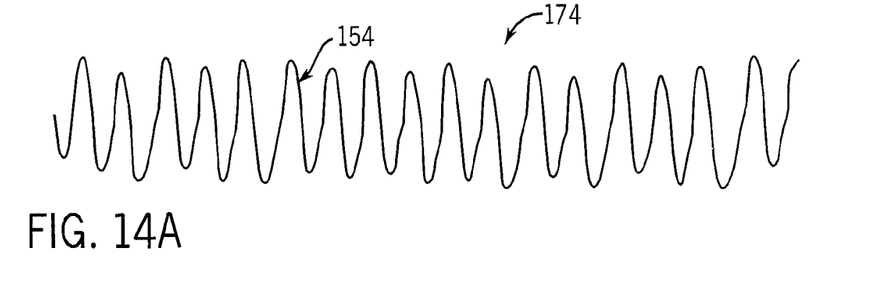
FIG. 14A is a diagram similar to FIG. 9, but illustrating ventricular tachycardia.
Figure 14B:
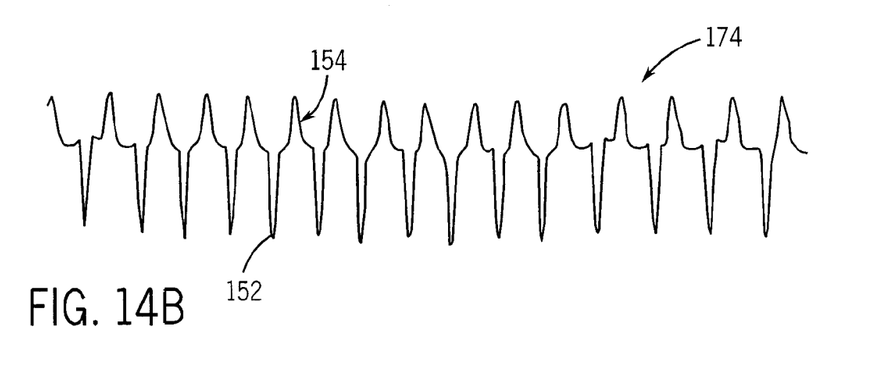
FIG. 14B is a diagram similar to FIG. 14A, but illustrating ventricular tachycardia with inverted P-waves.

Ventricular arrhythmias that affect the beating of the ventricles are more severe than those described above. Ventricular tachycardia occurs when electrical impulses originating from the ventricles cause rapid ventricular depolarization (e.g., 140-250 beats per minute). During ventricular tachycardia pumping blood is less efficient because the rapid ventricular contractions prevent the ventricles from filling adequately with blood. As a result, less blood is pumped to the body. The reduced blood flow to the body causes weakness, dizziness, and fainting. As illustrated in FIG. 14 A, the QRS complexes 154 of a ventricular tachycardia rhythm 174 are wide and chaotic. Alternatively, as illustrated in FIG. 14B, rhythm 174 can demonstrate inverted P-waves, resulting from ventricular impulses that are conducted backwards to the atria in some instances.

Figure 15:
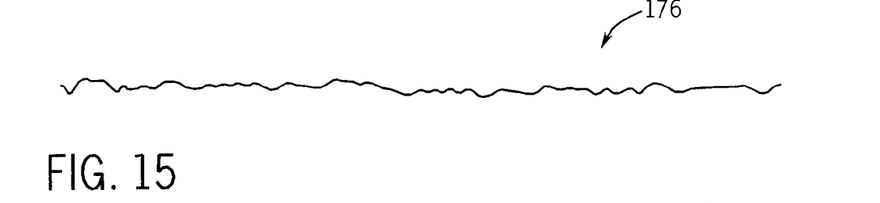
FIG. 15 is a diagram similar to FIG. 9, but illustrating ventricular fibrillation.

Ventricular fibrillation occurs when parts of the ventricles quiver and beat ineffectively in a chaotic, uncoordinated manner, thereby stopping the pumping action necessary to circulate blood throughout the body. The ECG in ventricular fibrillation shows random, apparently unrelated waves. Usually, as illustrated in FIG. 15, no QRS complex is recognizable in a ventricular fibrillation rhythm 176.

A prolonged Q-T interval also can, at times, indicate a potentially fatal arrhythmia if not treated, and can be detected by examining the Q-T intervals in recently acquired ECG data with Q-T intervals from baseline ECG data. For instance, a prolonged Q-T interval can be detected if the Q-T interval in recently acquired data reaches or exceeds a predetermined threshold greater than the baseline data.

After a suitable amount of data has been collected, analysis of the ECG signal for atrial fibrillation or other arrhythmia is begun using a predetermined method, as indicated by process block 54. Such methods are well known to those having ordinary skill in the art, as described in U.S. Pat. No. 5,350,404, the disclosure of which is hereby incorporated by reference. For instance, atrial fibrillation can be detected by measuring the time interval between adjacent R waves (the R-R interval). If the R-R interval is chaotic (meaning that the interval varies from interval-to-interval beyond a predetermined variance threshold well known in the art), then it is determined that the patient is experiencing atrial fibrillation.

Step 54 can also test for other cardiac arrhythmias. In particular, step 54 can test for atrial flutter by determining the presence of F waves in the acquired ECG data. Likewise, Bradycardia can be detected if the length of the R-R interval is greater than a preset threshold. The threshold can be determined based on the user's R-R interval during a normal ECG signal. Tachycardia can be determined by measuring the R-R interval (e.g., less than 0.6 seconds). Ventricular fibrillation can be detected from the nonexistence of a QRS complex. Ventricular tachycardia can be determined by comparing the shape of the QRS complexes to previously stored QRS complexes, which were acquired for the user during a period of normal ECG data. If the recently obtained QRS complexes are wide and chaotic compared to previously stored data, step 54 would determine that the user is experiencing ventricular tachycardia.

While methods have been described above to determine whether acquired ECG data demonstrates one of several possible cardiac arrhythmias, the present invention recognizes the advantages of redundancy, and hence can perform more than one method to determine the likelihood of an arrhythmia. In accordance with the preferred embodiment, a second method used to detect an arrhythmia involves comparing recently acquired ECG data with the previously stored sample baseline data described above. In particular, sample baseline data is acquired and modeled for a normal ECG signal along with each of the arrhythmias described above. Data from the acquired ECG signal is then compared to models associated with each of the normal ECG signal and arrhythmias, and a likelihood is determined, based on the comparison of the acquired data to the models, which of the previously generated models best matches the recently acquired ECG data. Based on the matched models, monitor 10 can determine whether an acquired ECG signal is normal, or that the ECG signal matches an arrhythmia. If either of the two methods for detecting an arrhythmia describe herein conclude that an arrhythmia exists, the patient will be alerted, as is described in more detail below. Alternatively, both methods would indicate a positive reading before it is determined at process block 54 that the patient is experiencing an arrhythmia.

Figure 16:
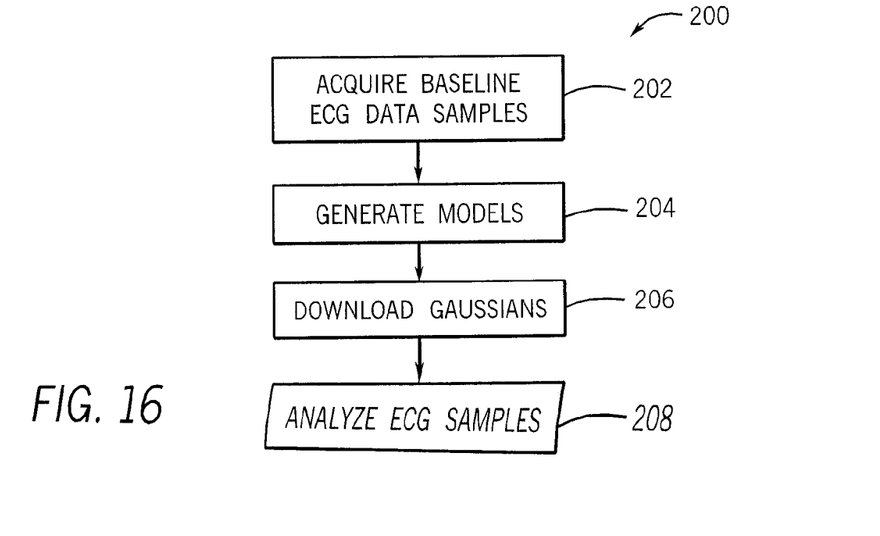
FIG. 16 is a flow chart illustrating steps to detect an arrhythmia.

Referring now to FIG. 16, the secondary arrhythmia detection method 200 can be included, and is preferably performed preparatory to a patient using monitor 10 for ECG analysis. Method 200 begins at step 202, whereby a plurality of baseline ECG data samples is acquired in a programming computer, which can be the same programming computer described above, or a central computer that can communicate via telephone with a plurality of monitors 10.

Each sample of data can either be of the patient (patient-dependent), or the data can be acquired from a pool of a predetermined number of patients (patient-independent) and averaged to derive a sample for a given rhythm class (i.e., normal data or a specific arrhythmia that is to be tested). The patient currently being tested need not be part of the pool that provides the patient-independent data. Because the likelihood of obtaining sample data from the patient for all conditions is low, and because patient-independent samples have been found to be robust and reliable during operation, patient-independent data samples are preferred. Data samples are preferably obtained for normal ECG data (i.e., data not exhibiting an arrhythmia), along with data samples for each arrhythmia that is to be tested for during operation.

Next, at step 204, a model is generated for each ECG rhythm including any and all of the arrhythmias listed above along with an arrhythmia-free ECG rhythm from the data samples. In particular, referring now to FIG. 17 at step 210, each data sample (which corresponds to a predetermined ECG rhythm) is first filtered through band pass filters several times to divide the signal into a plurality of sub-banded signals (between 1 and 10, more preferably between 4 and 6, and more preferably 4) based on the frequency range of each sub-banded signal. In accordance with the preferred embodiment, the four signals are divided into frequency ranges of 0.5-5 Hz, 5-10 Hz, 10-20 Hz, and 20-30 Hz, though it should be easily appreciated that any suitable set of frequency ranges could be used. Furthermore, each signal can be tagged, if desired, to maintain the identity of the signal.

Figure 17:
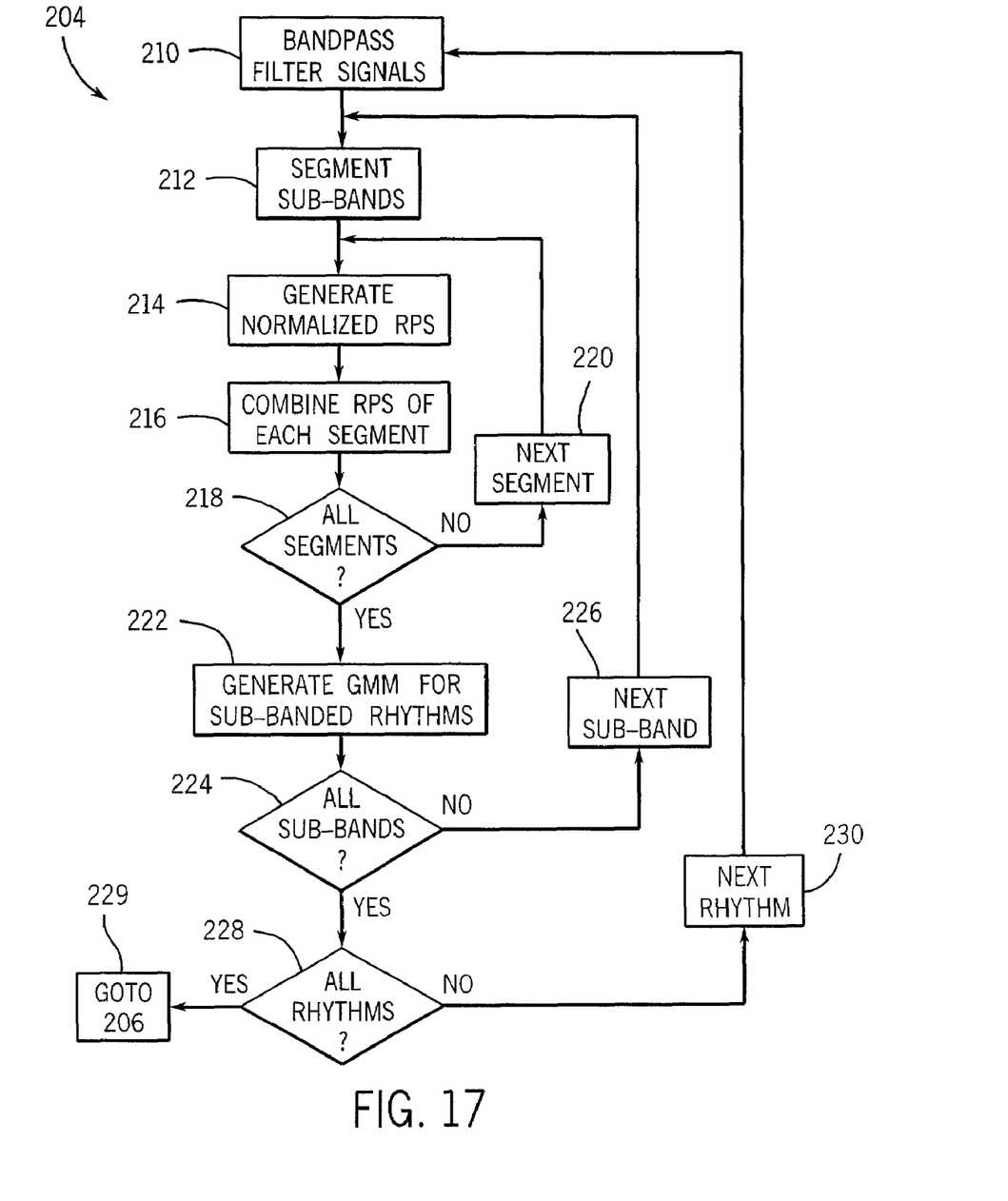
FIG. 17 is a flow chart illustrating the steps to generate a model of baseline data, as illustrated in FIG. 16.

At step 212, each sub-banded signal is segmented into a plurality segments of fixed lengths, the length being dependant upon the time period needed to enable accurate ECG assessment. It is desirable to reduce the length of the segment while, at the same time, enabling reliable data. In accordance with the preferred embodiment, the fixed segments are greater than one second, and more preferably equal to or greater than two seconds.

Next, at step 214, a reconstructed phase space (RPS) is generated for each segmented signal. The RPS is produced by plotting the original signal on an axis (e.g., the "x" axis) against multiple modified versions of the signal on other axes (e.g., the "y" and "z" axes). In accordance with the preferred embodiment, a modified signal is phase shifted relative to the original signal. The phase shift is preferably constant, and achieved by lagging behind the original signal by a predetermined fixed amount τ or multiples of τ (e.g., 2*τ). Phase shifted curves are produced in a multi-dimensional space, which has been empirically optimized as a 3-dimensional space with a lag of 20 data points in accordance with the preferred embodiment. Accordingly, the original segmented curve along with two phase-shifted curves are plotted in a 3-dimensional space (i.e., phase space). The multi-dimensional space is referred to herein as the reconstructed phase space.

At step 214, the phase space can optionally be normalized based, for example, on the average unit distance to the center of the phase space. Each sub-banded segment is normalized by dividing each point in the RPS by the average point radial distance in the RPS from the origin. The normalization removes the patient-independent differences in the amplitude of the signals. At step 216, the normalized RPS of the sub-banded segment is added to the RPS of the other sub-banded segments. Next, at decision block 218, it is determined whether the phase space has been produced and combined for all segments of the current rhythm. If not, the next segment is selected in block 220 and steps 210-216 are repeated for the next segment.

Once the phase space has been produced and combined for all segments of the rhythm, process 204 proceeds to step 222, whereby a Gaussian Mixture Model (GMM) is created for the combined RPS for all sub-banded RPSs of a given rhythm type. GMMs are well known in the art, and are described, for instance, in Richard J. Povinelli, Michael T. Johnson, Andrew C. Lindgren, Jinjin Ye. (2004) "Time Series Classification using Gaussian Mixture Models of Reconstructed Phase Spaces," IEEE Transactions on Knowledge and Data Engineering, vol. 16, no. 6, June, 779-783, the disclosure of which is hereby incorporated by reference as if set forth in its entirety herein.

In particular, a set of GMMs is produced that statistically model the density of points in the combined reconstructed phase space. In accordance with the preferred embodiment, twenty Gaussian equations are produced for a given phase space. Once the GMMs are produced for a given sub-banded phase space, it is determined at decision block 224 whether all the sub-bands for the desired rhythm have been modeled. If not, the next sub-band is selected at step 226, and steps 212-224 are repeated for all remaining sub-bands of the desired rhythm.

Once all sub-bands have been completed for a desired rhythm, it is determined at decision block 228 whether all desired rhythms have been modeled. If not, the next rhythm is selected at step 230, and steps 210-228 are repeated for all remaining rhythms. Once all rhythms including the arrhythmia-free rhythm have been modeled, process 204 proceeds to step 206 at step 229.

Referring again to FIG. 16, the GMMs for each rhythm are downloaded into monitor 10, and stored in nonvolatile memory 38 at step 206. Alternatively, GMMs could alternatively be downloaded into memory 38 upon completion of each individual rhythm. Next, referring to FIG. 18, monitor 10 performs an analysis 208 to determine whether ECG data for a patient exhibits an arrhythmia. In particular, at step 232, once ECG data is obtained for a given patient in the manner described above, microcontroller 10 band pass filters the acquired data into sub-bands in the manner described with respect to step 210. Next, at step 234, microcontroller 36 calculates a normalized phase space for the acquired data in the manner described above, and stores the phase space in volatile memory. Next, at step 236, microcontroller 36 compares the points that comprise the phase space calculated at step 234 to each GMM related to the sample baseline data for the current sub-band and calculates the probability that the acquired signal demonstrates a particular rhythm that was acquired at step 202 including the arrhythmia-free rhythm. Next, at decision block 238, it is determined whether all of the sub-bands have been analyzed. If not, the next sub-band is selected in block 240 and steps 234-238 are repeated for the next segment.

Figure 18:
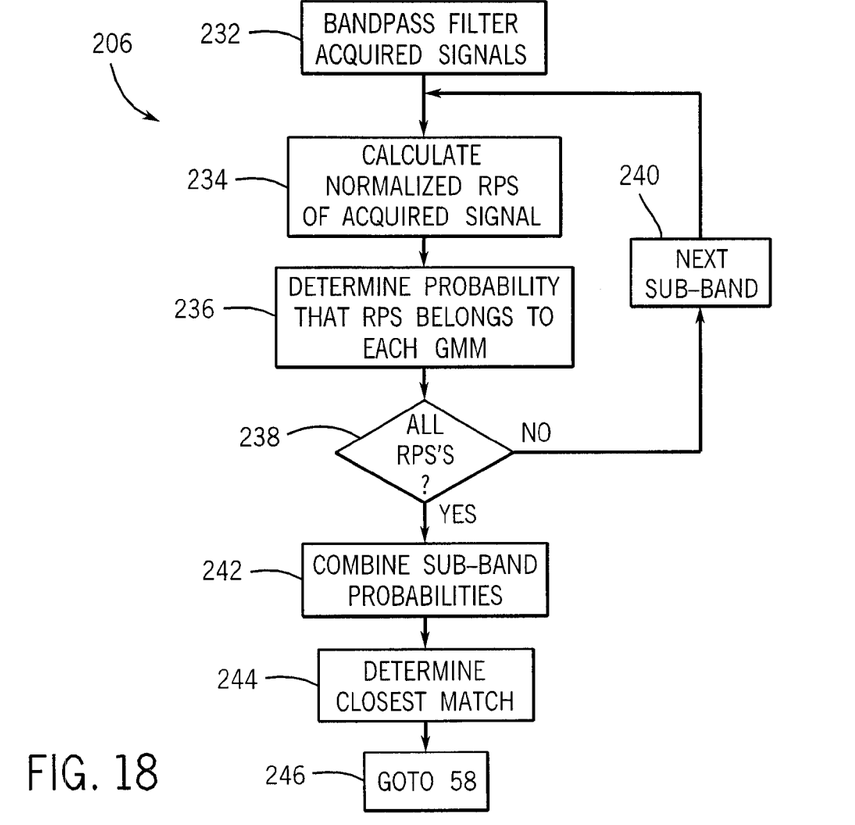
FIG. 18 is a flow chart illustrating the steps to analyze acquired ECG signals, as illustrated in FIG. 16.

At step 242, the probabilities calculated in step 236 are combined for each rhythm. At step 244, microcontroller 36 determines which set of GMMs most closely describes the points in the phase space calculated at step 242. In particular, at step 244, microcontroller 36 determines that the patient's recently acquired ECG sample is either normal or arrhythmatic (and if so, which arrhythmia is matched). At step 246, process 208 reverts to decision block 58 illustrated in FIG. 3.

Method 200 is further described in a publication entitled "Rhythm Classification Using Reconstructed Phase Space of Signal Frequency Sub-bands" by Felice M. Roberts, Richard J. Povinelli, and Kristina M. Ropella in Computers in Cardiology 2003, pp 61-64, the disclosure of which is hereby incorporated by reference as if set forth in its entirety herein.

Upon completion of the ECG signal analyses, an arrhythmia will be deemed to exist at decision block 58 when any of the methods described above indicate the existence of a cardiac arrhythmia. Advantageously, the present invention provides a redundant system for detecting arrhythmias, including atrial fibrillation, which is the most common arrhythmia among humans. If no arrhythmia was found by any of the methods, as determined by decision block 58, then the green indicator lamp 40 is illuminated and a text display may be provided to the patient via LCD display 30 indicating that no atrial fibrillation was found per process block 60. This outcome may be stored in memory 38 along with the ECG data and the memory 38 may hold ECG data and outcomes from previous measurements as a backup matter.

If an arrhythmia is detected then the program proceeds to process block 62 and the red indicator lamp 50 is illuminated. Lamp 50 can be illuminated in various patterns to convey a particular arrhythmia (or class of arrhythmias) to the patient. Alternatively still, a plurality of colored lights can be provided, each color corresponding to an individual arrhythmia or class of arrhythmias, such that illumination of a given light will alert the patient to the arrhythmia, or type of arrhythmia, that has been detected. Alternatively still, a text display can alert the user as to the detected arrhythmia.

With the indications of an arrhythmia, the patient may be instructed (or have been previously instructed) to call his or her physician and arrange for an in-office ECG to be taken.

Figure 4:
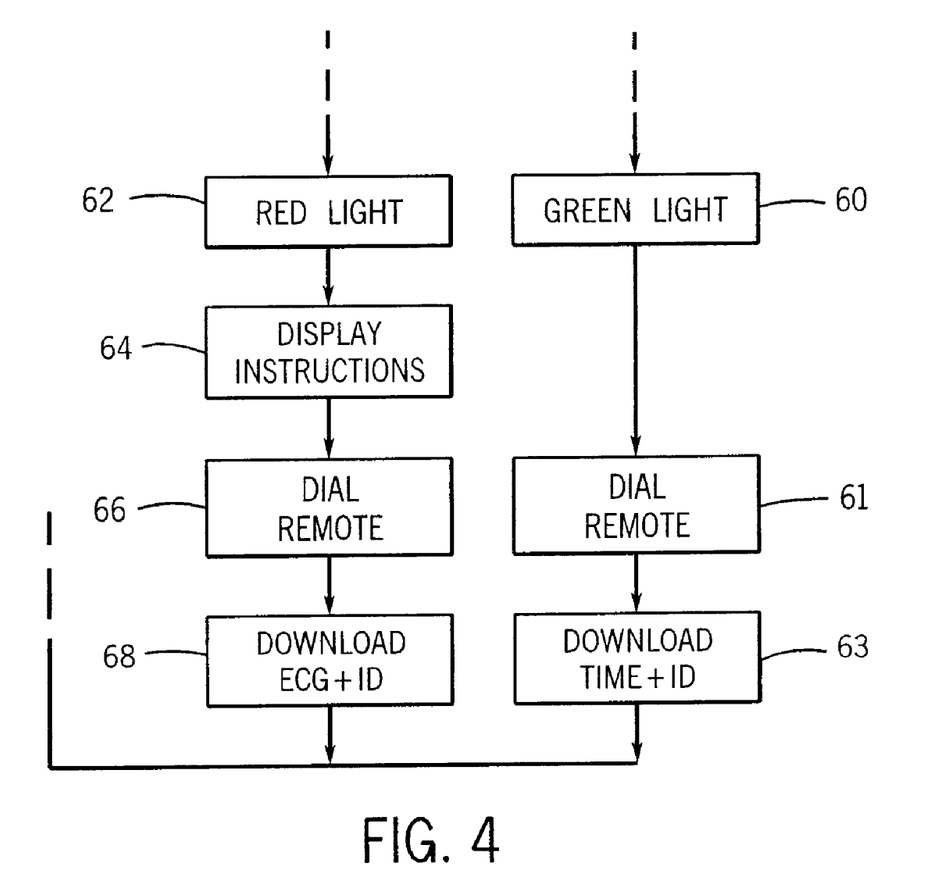
FIG. 4 is a flow chart similar to FIG. 5 showing additional steps taken for automatically downloading ECG data to a remote location for review.

Alternatively, as shown in FIG. 4, the microcontroller 36 may undertake additional steps after process blocks 60 and 62. Specifically, after the green light at process block 60 has been displayed, the microcontroller 36 may communicate with the modem 44 (or alternate communication system) to communicate with a central computer and report patient compliance in taking the measurement per process block 61. The transmitted data may include a time and a patient identification, the latter stored in memory 38 and preprogrammed there via the programming connector 17 prior to receipt of monitor 10 by the patient per process block 63. Optionally, the compliance signal may only be sent if a valid ECG signal was obtained.

When an arrhythmia is indicated at process block 62, instructions may be provided to the patient that data will be transmitted to a central location and the patient is to wait for a confirming phone call, per process block 64, or to call the patient's physician. At succeeding process block 66 the modem 44 or alternate communication system is activated, and at process block 68 a download of the data and the patient identification is sent to the central location. The data may be reviewed there by the patient's physician.

As described above, instead of a modem 44 linked to phone lines either directly or via an acoustic coupler, alternative communication systems may be used. For example, the ECG data may be transmitted to a personal computer for subsequent transmission to the central location via the Internet. The personal computers could further be used to store the ECG data either internally or on a storage medium such as a disc. Data may be communicated to the personal computer using one of many possible communication circuitries. For example, the monitor 10 may include a data transfer port, such as a Universal Serial Bus (USB), parallel, or serial port that is in communication with a corresponding port on the personal computer. Alternatively, the monitor may communicate with the computer via wireless communication, via, for example, an infrared communications link. Alternatively still, Bluetooth™ wireless technology may be implemented by installing a Bluetooth microchip incorporating a radio transceiver for communication with a corresponding Bluetooth microchip located in the personal computer.

Referring again to FIG. 2, the electrodes 24 may be spring-loaded to recess into the housing 12 slightly when pressed and thus may serve as operators for switches 25 communicating with the microcontroller 36 to provide a signal indicating that the device is being used (detected by process block 48) or to apply power to the device in the case where it is battery operated and power must be conserved. Either or both electrodes 24 may be thus connected to switches which may also be used to indicate to the user that the necessary pressure is being applied to the electrodes 24 for good electrical contact.

Figure 5A:
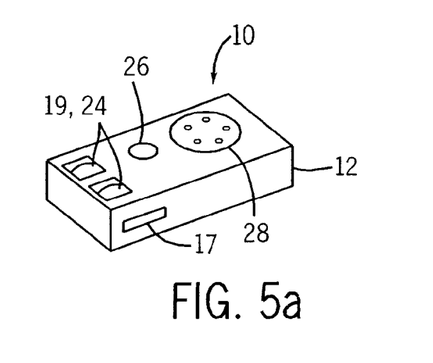
FIGS. 5a and 5b are views similar to that of FIG. 1 of an alternative embodiment for a compact atrial fibrillation device using finger pad electrodes or post electrodes instead of electrodes supported in handles.

Referring now to FIG. 5a, the goal of providing a convenient mechanism for long term monitoring of a patient for atrial fibrillation can also be met by a pocket sized unit having finger pads 19 also providing the electrodes 24 and operating on batteries so as to be set on a tabletop or be carried with the patient for travel. Of course, one skilled in the art will recognize that finger pads 19 can also be engaged by a patient's thumb(s). A phone connection may be provided through a direct modulation of the piezoelectric audio transducer 42 which may be held up to the telephone mouthpiece for use when the patient is at or away from home. The modulation technique in this case may be FM rather than the modem stile modulation of the modem 44 described above. The remote site may in this case include a provision for the patient providing a contact phone number at which the patient may be reached or may provide for the patient initiating a call with his or her physician or a contact number at the remote site.

Figure 5B:
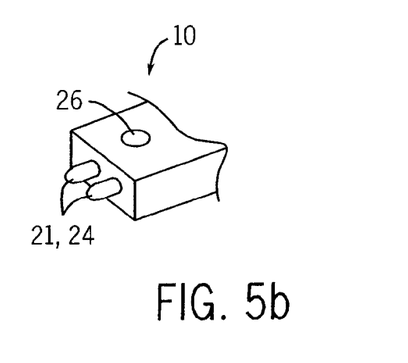

Referring now to FIG. 5b, as an alternative to the finger pads 19, posts 21 may be used spaced so as to be held against the patient's chest across the heart for a reading of ECG signals.

Figure 6:
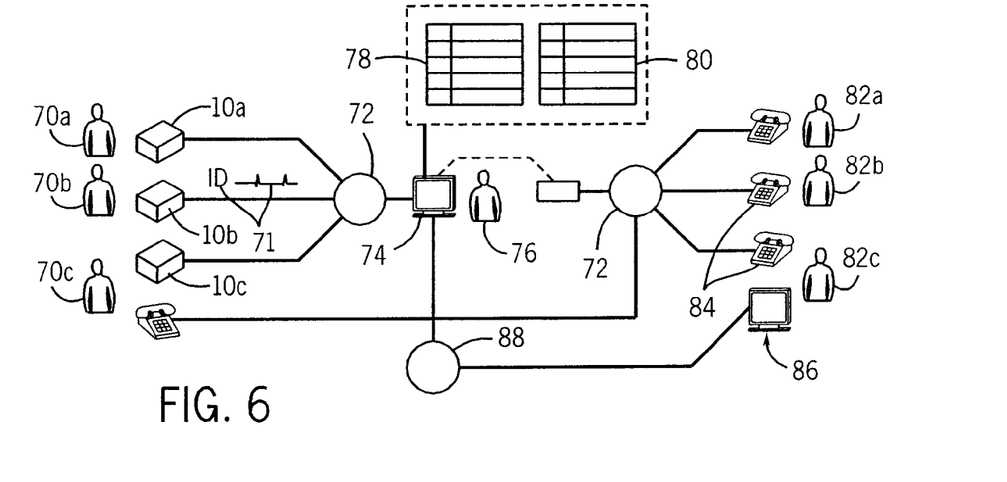
FIG. 6 is a diagram showing the path of information flow from the device to a central monitoring station for review by a qualified healthcare professional and later communication to the patient and/or the patient's physician.

Referring now to FIG. 6, a number of different patients 70a through 70c may each have a corresponding monitor 10a through 10c. At the regular time for patient monitoring, patient 70a through 70c may undertake the steps described above and patient identifications and/or ECG signals may be sent over the standard telephone network 72 from the monitors 10a through 10c to a central computer 74 having dial-up capabilities. It should be appreciated that network 72 could include a wireless network (e.g., via cellular technology).

At the central computer 74, a qualified healthcare professional 76 may monitor the transmissions 71 and, communicating with a physician-patient database 78 and a compliance database 80, manually or automatically make contact with various physicians 82a through 82c via standard telephone receivers 84 or computer terminals 86, the latter communicating with a web server 88. The physician-patient database 78 includes records linking particular patients, per patient identifications loaded into the monitors 10, to physicians responsible for those patients. The physician-patient database 78 may include phone numbers and e-mail addresses of the physicians and phone numbers of the patients whose use will be described below. The compliance database 80 includes records linking patients, per their identifications, to dates on which a compliance signal was received. As will be described, the system operates to make use of one or a limited number of qualified healthcare professionals 76 to verify the judgments of atrial fibrillation algorithm of the monitors 10a through 10c so as to only call physicians 82a through 82c if required, reducing any possible false alarms.

Figure 7:
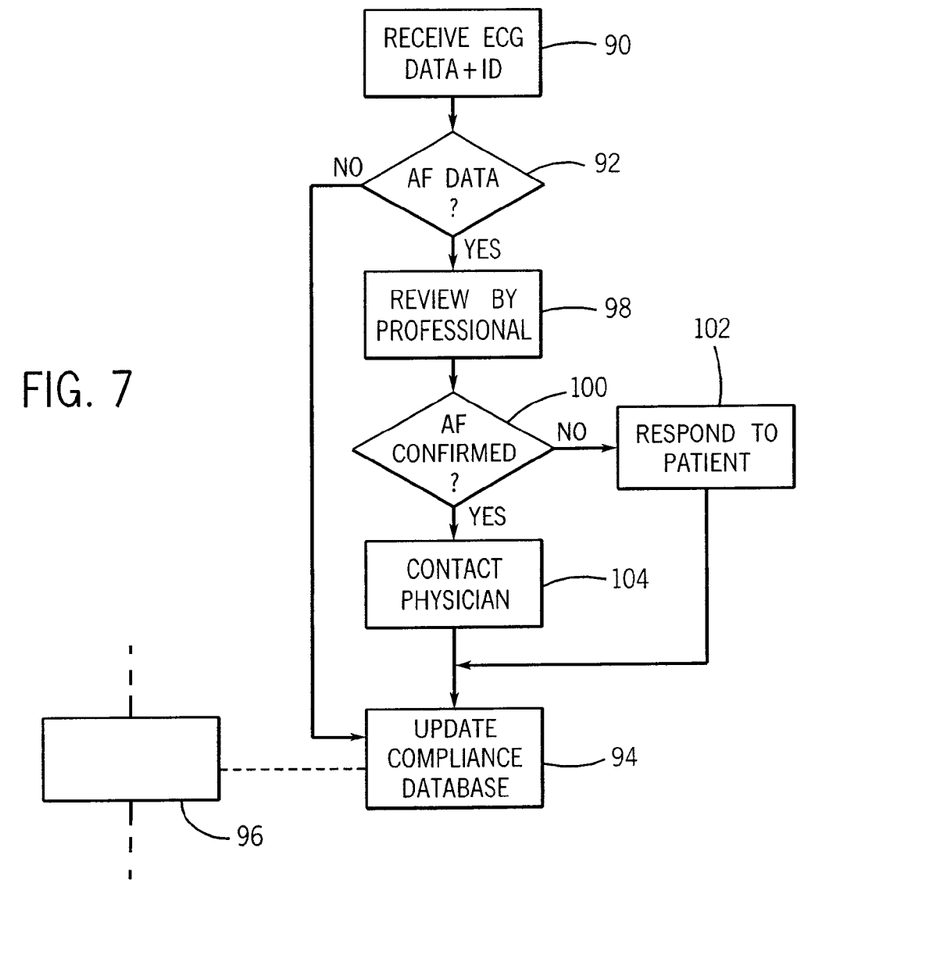
FIG. 7 is a flow chart showing operation of a computer of the central monitoring station in managing the information flow of FIG. 6.

Referring now to FIG. 7, generally, the computer 74 operates to receive ECG data and patient identification data as indicated by process block 90. At decision block 92 the data is automatically analyzed to see whether it is in response to a detection of a cardiac arrhythmia or is simply compliance data. If the data is compliance data, then the program proceeds to process block 94 and the patient compliance database 80 is updated as indexed by the patient identification transmitted along with the compliance data. If cascading memory scheme 51 is implemented, the data is stored in the oldest memory slot and tagged with identifying information, including the time of ECG acquisition along with an indication of normal or arrhythmatic ECG data along with, if applicable, an indication of the arrhythmia detected.

The data of the patient compliance database 80 may be posted to the web server 88 for review by the physician typically using a password protected review process. Alternatively, or in addition, a separate program 96 may periodically review the compliance database 80 to detect whether compliance is being had and if not, to send e-mail to the appropriate physician using the patient's identification to locate the proper physician using the physician-patient database 78.

Referring again to decision block 92, if cardiac arrhythmia data has been sent, that is, ECG data identified by the monitor 10 as exhibiting a cardiac arrhythmia, the ECG data is presented to the qualified healthcare professional 76 for a review as indicated by process block 98, including tag 55. The review may be by means of a standard computer monitor or may involve a printing out of the ECG data.

At decision block 100 the qualified healthcare professional 76 determines whether the cardiac arrhythmia is actually present. If the qualified healthcare professional 76 concludes that the transmitted ECG data shows a normal heartbeat (and that the monitor 10 was mistaken), then the program proceeds to process block 102 and the operator is presented, based on the patient identification associated with the data being displayed, with a phone number of the patient in the physician-patient database 78. The operator may then call the patient to indicate that there was no cardiac arrhythmia so that the patient need no longer wait by the phone. Alternatively, this message may be generated electronically through computer techniques well known in the art upon command by the qualified healthcare professional 76.

Referring again to decision block 100, if a cardiac arrhythmia is shown by the ECG data, after instruction by the qualified healthcare professional 76, the program proceeds to process block 104 and the qualified healthcare professional 76 is provided with the physician's phone number from the physician-patient database 78. The qualified healthcare professional 76 may then call a particular physician 82a through 82c to note that their patient has a confirmed cardiac arrhythmia (e.g., an episode of atrial fibrillation) and to instruct the doctor to review the ECG signals that have been posted to the web server 88. Alternatively, or in addition, an e-mail message may be submitted to the doctor attaching the ECG data as a graphics file according to techniques well known in the art. Again, this message may be provided automatically either by synthesized voice over a standard telephone network or by e-mail message.

In this way, a machine-diagnosed cardiac arrhythmia may be confirmed by a single highly experienced individual, shared among many patients, and a physician need only be brought into the loop when the arrhythmia has been confirmed.

In accordance with an alternate embodiment of the invention, monitor 10 can be worn on a patient's person. For instance, referring to FIGS. 19, monitor 10 can be connected to a strap 47 that can be fastened around a patient's wrist or waist. It should be further appreciated that monitor 10 could be integrated into a wristwatch.

The electrodes 24 can be configured as described above with reference to FIGS. 4 and 5 and the alternatives described herein. Alternatively, monitor 10 can provide virtual momentary contact electrodes 24, one of which extending outwardly away from the patient, the other of which extending inwardly from monitor 10 so as to be in constant contact with the patient's skin. The outwardly facing electrode 24 is engaged by a user's hand to begin data acquisition. Alternatively still, both electrodes could face inwardly to be in constant contact with the patient, and the microcontroller 36 would sample the patient's ECG data at predetermined time intervals upon the expiration of a preset timer. A manual override (not shown) can be provided on the face of monitor 30 in the form of a button or the like that the patient would activate to initiate ECG data acquisition regardless of the time interval. Because only momentary data is acquired by the user-worn monitor 10 having electrodes 24 in any of the configurations described above (e.g., one or more times per day) as opposed to constant ECG sampling, the electrodes are referred to herein as momentary contact electrodes.

The patient-worn monitor 10 includes the components illustrated in FIG. 2. However, modem 44 is replaced with a communications module using Bluetooth™ wireless technology by installing a Bluetooth microchip incorporating a radio transceiver for communication with a corresponding Bluetooth microchip located in the personal computer. Alternatively, module 44 can communicate with the personal computer using infrared or any alternative well-known wireless technology.

Figure 19:
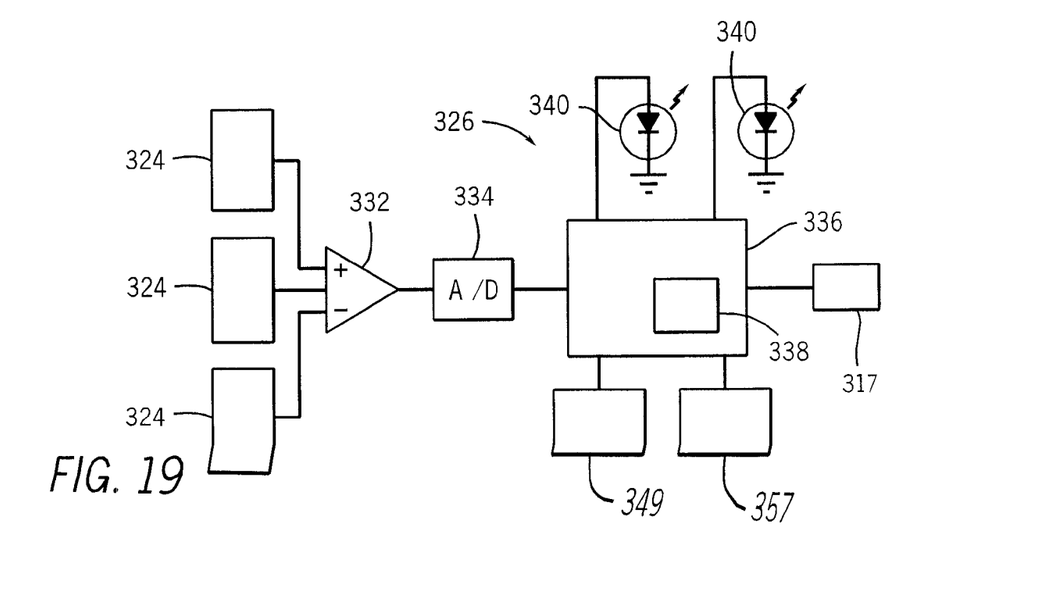
FIG. 19 is a block diagram of the components of an ECG monitor constructed in accordance with an alternate embodiment.

The present invention further recognizes that advantages may be achieved using multiple arrhythmia detection methods in combination with an ECG monitor that does not include momentary contact electrodes, but rather uses permanent electrodes to continuously monitor a patent's ECG signal (hereinafter referred to as a "permanent ECG monitor"). The components of permanent monitor 310 are illustrated in FIG. 19, and include reference numerals corresponding to like elements of monitor 10 (illustrated in FIG. 2) incremented by 300 for the purposes of clarity and convenience. In particular, multiple channels of data may be obtained by attaching multiple contact electrodes 324 to the patient in the known manner. For example, one contact electrode can be placed on the patients left arm, another placed on the patients right arm, and a third electrode placed on the patients abdomen or one of the patient's legs so that the electrodes form a triangle. Three channels of ECG data may thus be obtained (each channel originating from adjacent electrodes).

The multiple channels of ECG data are amplified by a corresponding one or more amplifiers 332, and fed into a corresponding one ore more analog to digital converters 334. Only one amplified 332 and converter 334 is illustrated in FIG. 19. The output from converter(s) 324 is sent to a microcontroller 336, including volatile and nonvolatile memory 338. Controller 336 is connected to a programming connector 317, and one or more indicator lights 326.

A detector circuit of the type described above is thus connected to each channel of data, such that the permanent ECG monitor can then determine which channel exhibits R peaks of the greatest amplitude, and analyze the R-R interval of that channel to determine whether any R-R interval-dependent arrhythmias exist using the methods described above. Alternatively, any channel may be selected having an R peak greater than a predetermined amplitude. The other channel (or possibly the other two channels) can be analyzed using method 200. Redundancy is thus achieved in the event that one of the contact electrodes is not adequately connected to the patient. Furthermore, the implementation of two arrhythmia detection methods achieves the benefits described above with reference to the momentary contact electrodes.

During operation, the permanent ECG monitor continuously reads ECG data from the patient, and stores data from an immediately previous time frame (e.g., the previous 2 minutes of ECG data) in volatile memory. The old data in volatile memory is thus constantly being overwritten with new data. If the monitor determines, based on either or both arrhythmia detection methods, that the patient is experiencing an arrhythmia, an alarm can be activated on a display 357 (or by any other suitable means), and the data residing in the volatile memory can be captured and stored in nonvolatile memory 338 for future retrieval by the attending physician. Data can also be captured from volatile memory and stored into nonvolatile memory upon the activation of a button, switch, or the like 349, when the patient exhibits a symptom of a cardiac arrhythmia.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. A method for detecting a likelihood that a patient is experiencing one of several arrhythmias, the method comprising the steps of:

(a) acquiring baseline ECG samples, each of which exhibiting an arrhythmia to be detected and a baseline arrhythmia-free ECG sample;

(b) segmenting each sample into a fixed length;

(c) mapping a reconstructed phase space related to each acquired baseline ECG sample;

(d) determining at least one model describing the reconstructed phase space for each acquired baseline ECG sample;

(e) acquiring an ECG sample to be tested;

(f) segmenting the ECG sample to be tested into a fixed length;

(g) mapping each segment of the ECG sample into a reconstructed phase space related to the ECG sample to be tested; and (h) determining which of the models of the reconstructed phase space of the baseline ECG samples most accurately describes the reconstructed phase space related to the ECG sample to be tested.

2. The method as recited in claim 1, further comprising:
(i) determining that the ECG sample to be tested is arrhythmia-free if the phase space related to the ECG sample to be tested is most accurately described by the equation describing the baseline arrhythmia-free ECG sample.

3. The method as recited in claim 1, further comprising:
(i) determining that the ECG sample to be tested exhibits an arrhythmia if the phase space related to the ECG sample to be tested is most accurately described by the equation describing the arrhythmia.

4. The method as recited in claim 1, wherein step (c) further comprises filtering the acquired baseline ECG samples.

5. The method as recited in claim 4, wherein the filtering comprises band-pass filtering.

6. The method as recited in claim 1, wherein step (c) further comprises dividing each ECG sample into a plurality of bands.

7. The method as recited in claim 1, wherein step (d) further comprises producing at least one Gaussian equation describing the phase shift.

8. The method as recited in claim 1, wherein step (g) further comprises filtering the ECG sample to be tested.

9. The method as recited in claim 8, wherein the filtering comprises band-pass filtering.

10. The method as recited in claim 8, wherein step (g) further comprises dividing each ECG sample into a plurality of bands.

11. The method as recited in claim 1, wherein step (h) further comprises matching locations within the phase space of the acquired ECG sample to be tested with each equation describing the phase space of the acquired baseline ECG sample.

12. The method of claim 1 further comprising:
(i) determining that the ECG sample to be tested includes indicia of an arrhythmia if the phase space mapped to the ECG sample is most accurately described by a model mapped to a baseline ECG sample exhibiting an arrhythmia; and
(j) determining that the ECG sample to be tested includes indicia of being arrhythmia-free if the phase space mapped to the ECG sample is most accurately described by a model mapped to the baseline arrhythmia-free EGG sample.

13. The method of claim 1 wherein step (b) further comprises band-pass filtering the acquired baseline ECG samples into a plurality of frequency sub-bands, step (c) further comprises mapping a reconstructed phase space related to each acquired, band-pass filtered baseline ECG sample, step (f) further comprises band-pass filtering the ECG sample into a plurality of frequency sub-bands, step (g) further comprises mapping each band-pass filtered ECG sample to be tested into a reconstructed phase space, and step (h) further comprises determining which if the models of the reconstructed phase space of band-pass filtered baseline ECG samples most accurately descries the reconstructed phase space related to the ECG sample to be tested.

14. The method of claim 13 wherein step (d) further comprises producing at least one mixture Gaussian mixture model describing the reconstructed phase space of the band-pass filtered baseline ECG sample.

15. A method for detecting a likelihood that a patient is experiencing one of several arrhythmias, the method comprising the steps of:
(a) acquiring baseline ECG samples, each of which exhibiting an arrhythmia to be detected and a baseline arrhythmia-free ECG sample;
(b) mapping a reconstructed phase space related to each acquired baseline ECG sample;
(c) determining at least one equation describing the reconstructed phase space for each acquired baseline ECG sample;
(d) acquiring an ECG sample to be tested;
(e) mapping a reconstructed phase space related to the ECG sample to be tested;
(f) determining which of the equations most accurately describes the reconstructed phase space related to the ECG sample to be tested;
wherein step (b) further comprises dividing each ECG sample into a plurality of bands;
wherein step (b) further comprises segmenting each band to a fixed length; and
wherein step (b) further comprises plotting each band against more than one phase shift of the plotted band.

16. A method for detecting a likelihood that a patient is experiencing one of several arrhythmias, the method comprising the steps of:
(a) acquiring baseline ECG samples, each of which exhibiting an arrhythmia to be detected and a baseline arrhythmia-free ECG sample;
(b) mapping a reconstructed phase space related to each acquired baseline ECG sample:
(c) determining at least one equation describing the reconstructed phase space for each acquired baseline ECG sample;
(d) acquiring an ECG sample to be tested;
(e) mapping a reconstructed phase space related to the ECG sample to be tested;
(f) determining which of the equations most accurately describes the reconstructed phase space related to the ECG sample to be tested;
wherein step (e) further comprises filtering the ECG sample to be tested;
wherein step (e) further comprises segmenting each band to a fixed length; and
wherein step (e) further comprises plotting each band against more than one phase shift of the plotted band.

17. A method for detecting a likelihood that a patient is experiencing one of several arrhythmias, the method comprising the steps of:
(a) acquiring baseline ECG samples, each of which exhibiting an arrhythmia to be detected and a baseline arrhythmia-free ECG sample;
(b) mapping a reconstructed phase space related to each acquired baseline ECG sample;
(c) determining at least one equation describing the reconstructed phase space for each acquired baseline ECG sample;
(d) acquiring an ECG sample to be tested;
(e) mapping a reconstructed phase space related to the ECG sample to be tested; and
(f) determining which of the equations most accurately describes the reconstructed phase space related to the ECG sample to be tested; and
wherein steps (a) through (f) comprises a first detection method of determining the likelihood that the patient is experiencing one of several arrhythmias, further comprising the step of:
(g) using a second detection method to determine a second likelihood that the patient is experiencing the arrhythmia.

18. An apparatus for detecting a likelihood that a patient is experiencing one of several arrhythmias, the apparatus comprising:
(a) means for acquiring baseline ECG samples, each of which exhibiting an arrhythmia to be detected and a baseline arrhythmia-free ECG sample;
(b) means for segmenting each baseline ECG sample into a fixed lenght;
(c) means for dividing each baseline ECG sample into a plurality of frequency sub-bands;
(d) means for mapping a reconstructed phase space related to each frequency sub-band of the baseline ECG sample;
(e) means for determining at least one model describing the reconstructed phase space for each frequency sub-band of the baseline ECG sample;
(f) means for acquiring an ECG sample to be tested;
(g) means for segmenting each ECG sample to be tested into a fixed length;
(h) means for dividing each ECG sample to be tested into a plurality of frequency sub-bands;
(i) means for mapping a reconstructed phase space related to each frequency sub-band of the ECG sample to be tested; and
(j) means for determining which of the modeled baseline ECG samples most accurately describes the reconstructed phase space related to the ECG sample to be tested.

19. The apparatus as recited in claim 18, further comprising:
(k) means for determining a second likelihood that the patient is experiencing an arrhythmia.

20. The apparatus as recited in claim 19, wherein the (e) means for determining further comprises means for producing at least one mixture Gaussian mixture model describing the reconstructed phase space of the baseline ECG samples.

21. The apparatus as recited in claim 18, further comprising:
(k) means for determining that the ECG sample to be tested exhibits an arrhythmia if the phase space related to the ECG sample to be tested is most accurately described by the equation describing the arrhythmia.

22. The apparatus as recited in claim 18, wherein the first means for mapping further comprises means for filtering the acquired baseline ECG samples.

23. The apparatus as recited in claim 22, wherein the filtering comprises band-pass filtering.

24. The apparatus as recited in claim 18, wherein the first means for mapping further comprises means for dividing each ECG sample into a plurality of bands.

25. The apparatus as recited in claim 18, wherein the first means for mapping further comprises means for plotting each band against more than one phase shift of the plotted band.

26. The apparatus as recited in claim 18, wherein the second means for determining comprises means for matching locations within the phase space of the acquired ECG sample to be tested with each equation describing the phase space of the acquired baseline ECG sample.

27. An apparatus for detecting a likelihood that a patient is experiencing one of several arrhythmias, the apparatus comprising:
(a) means for acquiring baseline ECG samples, each of which exhibiting an arrhythmia to be detected and a baseline arrhythmia-tree ECG sample;
(b) means for mapping a reconstructed phase space related to each acquired baseline ECG sample;
(c) means for determining at least one equation describing the reconstructed phase space for each acquired baseline ECG sample;
(d) means for acquiring an ECG sample to be tested;
(e) means for mapping a reconstructed phase space related to the ECG sample to be tested;
(f) means for determining which of the equations most accurately describes the reconstructed phase space related to the ECG sample to be tested; and
wherein the first means for determining further comprises means for producing at least one Gaussian equation describing the phase shift.

28. An apparatus for detecting a likelihood that a patient is experiencing one of several arrhythmias, the apparatus comprising:
(a) means for acquiring baseline ECG samples, each of which exhibiting an arrhythmia to be detected and a baseline arrhythmia-free ECG sample;
(b) means for mapping a reconstructed phase space related to each acquired baseline ECG sample;
(c) means for determining at least one equation describing the reconstructed phase space for each acquired baseline ECG sample;
(d) means for acquiring an ECG sample to be tested;
(e) means for mapping a reconstructed phase space related to the ECG sample to be tested;
(f) means for determining which of the equations most accurately describes the reconstructed phase space related to the ECG sample to be tested; and
wherein the second means for mapping comprises means for filtering the ECG sample to be tested.

29. The apparatus as recited in claim 28, wherein the filtering comprises band-pass filtering.

30. The apparatus as recited in claim 28, wherein the second means for mapping further comprises means for dividing each ECG sample into a plurality of bands.

31. The apparatus as recited in claim 28, wherein the second means for mapping further comprises means for segmenting each band to a fixed length.

32. The apparatus as recited in claim 31, wherein the second means for mapping further comprises means for plotting each band against more than one phase shift of the plotted band.

* * * * *